(12) United States Patent
Visuri et al.

(10) Patent No.: US 6,538,739 B1
(45) Date of Patent: *Mar. 25, 2003

(54) BUBBLE DIAGNOSTICS

(75) Inventors: Steven R. Visuri, Livermore; Beth M. Mammini, Walnut Creek; Luiz B. Da Silva, Danville; Peter M. Celliers, Berkeley, all of CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 362 days.

(21) Appl. No.: 08/941,015

(22) Filed: Sep. 30, 1997

(51) Int. Cl.$^7$ .............................................. G01B 11/00
(52) U.S. Cl. ......................... 356/394; 356/388; 356/372
(58) Field of Search ................. 356/394, 388, 356/372

(56) References Cited

U.S. PATENT DOCUMENTS

| | | | |
|---|---|---|---|
| 4,240,747 A | * 12/1980 | Harmon | 356/133 |
| 4,300,689 A | * 11/1981 | Franklin et al. | 356/407 |
| 4,504,727 A | 3/1985 | Melcher et al. | |
| 4,641,650 A | 2/1987 | Mok | |
| 4,662,749 A | 5/1987 | Hatton et al. | 356/336 |
| 4,718,417 A | 1/1988 | Kittrell et al. | 128/303.1 |
| 4,862,886 A | 9/1989 | Clarke et al. | |
| 4,939,336 A | 7/1990 | Meyer | |
| 4,986,659 A | 1/1991 | Bachalo | 356/336 |
| 5,017,775 A | 5/1991 | Granz et al. | 250/227.25 |
| 5,158,560 A | 10/1992 | Sogawa et al. | |
| 5,163,432 A | 11/1992 | Ueno et al. | 128/660.03 |
| 5,254,112 A | 10/1993 | Sinofsky et al. | |
| 5,254,114 A | 10/1993 | Reed, Jr. et al. | |

(List continued on next page.)

FOREIGN PATENT DOCUMENTS

| | | |
|---|---|---|
| EP | 194856 B1 | 5/1992 |
| EP | 572435 B1 | 5/1995 |
| WO | 9007904 | 7/1990 |
| WO | 9214415 | 9/1992 |

OTHER PUBLICATIONS

Scheu et al., "A New Concept for a Realtime Feedback System in Angioplasty with a Flashlamp Pumped Dye Laser," Lasers in Surgery & Medicine, vol. 11, pp. 133–140 (1991).

Ansari et al, "Fiber–Optic Refractive–Index Sensor for use in Fresh Concrete," Applied Optics, vol. 30, No. 28 (Oct. 1991), pp. 4056–4059.

Hussein, "A Novel Delivery System for Laser Thermal Recanalization," 1989, 11th Int'l Conference, IEEE Engineering in Medicine & Biology Society (Abstract).

*Primary Examiner*—Frank G. Font
*Assistant Examiner*—Michael P. Stafira
(74) *Attorney, Agent, or Firm*—John P. Wooldridge; Alan H. Thompson

(57) ABSTRACT

The present invention is intended as a means of diagnosing the presence of a gas bubble and incorporating the information into a feedback system for opto-acoustic thrombolysis. In opto-acoustic thrombolysis, pulsed laser radiation at ultrasonic frequencies is delivered intraluminally down an optical fiber and directed toward a thrombus or otherwise occluded vessel. Dissolution of the occlusion is therefore mediated through ultrasonic action of propagating pressure or shock waves. A vapor bubble in the fluid surrounding the occlusion may form as a result of laser irradiation. This vapor bubble may be used to directly disrupt the occlusion or as a means of producing a pressure wave. It is desirable to detect the formation and follow the lifetime of the vapor bubble. Knowledge of the bubble formation and lifetime yields critical information as to the maximum size of the bubble, density of the absorbed radiation, and properties of the absorbing material. This information can then be used in a feedback system to alter the irradiation conditions.

61 Claims, 8 Drawing Sheets

U.S. PATENT DOCUMENTS

| | | |
|---|---|---|
| 5,263,361 A | 11/1993 | Gates .................... 73/45.5 |
| 5,269,778 A | 12/1993 | Rink et al. |
| 5,377,683 A | 1/1995 | Barken |
| 5,447,509 A | 9/1995 | Mills et al. |
| 5,455,423 A | 10/1995 | Mount et al. ............. 250/343 |
| 5,472,406 A | 12/1995 | de la Torre et al. ......... 601/2 |
| 5,473,136 A | 12/1995 | Engelhardt et al. ..... 219/121.62 |
| 5,601,738 A | 2/1997 | Engelhardt et al. |
| 5,662,590 A | 9/1997 | de la Torre et al. ......... 601/2 |
| 6,033,371 A | 3/2000 | de la Torre et al. ......... 601/2 |
| 6,106,546 A | 8/2000 | Gregory .................. 607/89 |

* cited by examiner

BUBBLE DIAGNOSTICS

The United States Government has rights in this invention pursuant to Contract No. W-7405-ENG-48 between the United States Department of Energy and the University of California for the operation of Lawrence Livermore National Laboratory.

BACKGROUND OF THE INVENTION

Field of the Invention

The present invention relates to the use of lasers to produce acoustic signals in liquid media, and more specifically, it relates to systems for diagnosing the presence of a gas bubble in liquid media.

Description of Related Art

In U.S. Pat. No. 4,986,659, titled "Method For Measuring The Size And Velocity Of Spherical Particles Using The Phase And Intensity Of Scattered Light," an improved apparatus and method for determining the change in the effective cross-section of a sample volume defined by two crossed laser beams is disclosed. A laser generation means is provided for generating a pair of coherent laser beams and means are provided to change the separation, intersection angle, and focused diameter of the beams. These beams are directed along an axis, and are caused to cross the axis at a given angle to define an interference pattern constituting a sample volume. A collection apparatus for sensing the scattering of light caused by particles, droplets, bubbles, or the like within the sample volume is provided. In the presently preferred embodiment, the collection apparatus is disposed at preferred off-axis angles including off-axis backscatter with the angle predetermined, and the angle defined by the direction of beam propagation. The collected scattered light is directed onto photo-detectors which are coupled to a signal phase determining means, for measuring the relative phase between the signals produced by each photo-detector and a signal amplitude determining means to measure the relative amplitude of the signals produced as the particle, drop, bubble, or the like passes through the sample volume. Sizing means are coupled to the signal phase and amplitude determination means for determining the size of the particle, drop, bubble, or the like from phase and amplitude changes in the received signals. Methods and apparatus are disclosed for determining the change in the effective cross-section of the sample volume due to size variations of particles passing through the interference pattern. The velocity of the particle drop, bubble, or the like is determined using well known laser Doppler anemometry techniques.

U.S. Pat. No. 5,263,361, titled "Apparatus For Leak Testing A Fluid Containing Chamber Utilizing A Laser Beam" is directed to a method and apparatus for leak testing a fluid containing chamber wherein the chamber is pressurized with a gas and is submerged in a liquid. The bubbles of gas rising from the submerged chamber are directed past a plurality of a predetermined locations that are each in optical communication with a photoelectric detector. The signals from the detectors are counted and when the number of bubbles exceeds a predetermined number, a signal is activated indicating a leaking container. By grouping a number of adjacent photoelectric detectors into a predetermined set, the apparatus can discriminate between random bubbles rising from the chamber surface as it is submerged and a number of bubbles all originating from a given location indicating a leak. The photoelectric detectors may be positioned in the liquid adjacent the predetermined locations or positioned out of the liquid and coupled to the predetermined locations by fiber optic cables. Alternatively, a laser beam can be directed across the predetermined location and received by a detector on the opposite side of the laser source. When a bubble interrupts the laser beam, a signal is generated.

U.S. Pat. No. 4,662,749, titled "Fiber Optic Probe And System For Particle Size And Velocity Measurement" discloses a system for the simultaneous measurement of the size and velocities of bubbles or drops in a multiphase process environment wherein light passing through a Ronchi grating is projected onto a measurement volume within the multiphase process stream by a coherent fiber optic bundle and a gradient index imaging lens. Drops or bubbles passing through the measurement volume reflect or refract light which is sensed by velocity and size sensor fiber optic bundles disposed opposite the imaging lens and the sensed signal is coupled to signal processing means which convert the light signal to electrical signals. The appropriate size velocity measurements are made using one or more of the visibility techniques, phase lag techniques or transit time techniques.

U.S. Pat. No. 5,473,136, titled "Method And Apparatus For The Machining Of Material By Means Of A Laser" discloses a method for the machining of material using a laser with detection of the material to be machined, where laser light is directed at the material via a laser optical system and the light re-emitted by the material is guided to a first detector arrangement which measures the intensity of the light and behind which there is connected an evaluation circuit for controlling the laser power or energy. The energy fed to the material via the laser optical system is measured, and the detector arrangement supplies to the evaluation circuit a display signal which indicates the beginning of the dielectric breakdown. The evaluation circuit reduces the power of the laser and/or interrupts the laser pulse if no display signal has as yet occurred at a predetermined time at which a predetermined energy was fed to the material.

SUMMARY OF THE INVENTION

It is an object of the present invention to provide an optical based method of detecting the presence of a vapor bubble.

It is another object of the invention to produce a signal which indicates the presence of a vapor bubble.

Still another object of the invention is to provide a feedback system for control of laser pulses used for bubble formation.

A light source such as a laser is coupled into an optical fiber and transmitted to the desired origin of bubble formation. The light reflected back into the distal fiber tip is monitored as it returns and is emitted out of the proximal end of the fiber. As a bubble forms at the distal end, the amount of reflected light increases as the index of refraction mismatch increases ($n_{fiber}-n_{air}>n_{fiber}-n_{liquid}$). This signal can yield information about the bubble and irradiated material such as time of bubble formation and collapse, size of bubble, absorption characteristics of the material, and mechanical characteristics of the material. This data can be used in a feedback control system for optimizing irradiation conditions. The invention may be used in a variety of applications including remote detection of cavitation or vaporization of target material as a result of laser irradiation. It may be used in hospitals in conjunction with laser based methods of stroke treatment and can be used for remote bubble detection in a variety of experiments where bubbles are formed, particularly at the end of an optical fiber.

DETAILED DESCRIPTION OF THE INVENTION

Although this invention may be used for a variety of bubble detection applications, it is discussed in light of medical applications, where a bubble is formed at a remote location within the body. Many bubble detection methods exist but are impractical for this application. Optical methods have been used to detect bubbles, often collecting light from the side opposite to the emission signal. In the present invention, light may be delivered and collected from the same optical fiber, eliminating the need to cross an occlusion and allowing for remote and minimally invasive access. Further, the same optical fiber used for delivering therapeutic radiation can be used for the bubble detection mechanism.

This invention incorporates a beam from a light source, such as a HeNe laser beam or diode laser beam, that is coupled into an optical fiber via a lens and directed to the site of bubble formation. This diagnostic beam can use the same optical fiber used by a second laser beam for bubble generation. Some of the diagnostic light emerging from the distal end of the fiber will be coupled back into the fiber through reflection and scattering. The light reflected directly back into the fiber is dependent on the change in refractive index between the fiber, n1, and the material at the distal end, n2, where the fraction of reflected light $R=|(n2-n1)/(n2+n1)|^2$. In addition, some light is scattered back into the fiber, depending on the optical properties, (scattering coefficient, absorption coefficient, and anisotropy), of the material at the distal end. This reflected and scattered feedback light is measured at the proximal end of the same fiber, allowing remote access to the treated area. As a bubble develops, the intensity of the feedback light changes. The DC level of the measured signal depends on the material at the output of the fiber. The AC component of the signal corresponds to the bubble dynamics. Time of growth and collapse, and the size of the generated bubble or bubbles, can be determined. Because the feedback signal is dependent on the material's optical properties, feedback signals at multiple wavelengths can be used as a method for identifying different types of tissue. This information can be incorporated into a feedback system, as discussed above, that controls and adjusts the irradiation parameters of the treatment laser.

Figure 1:
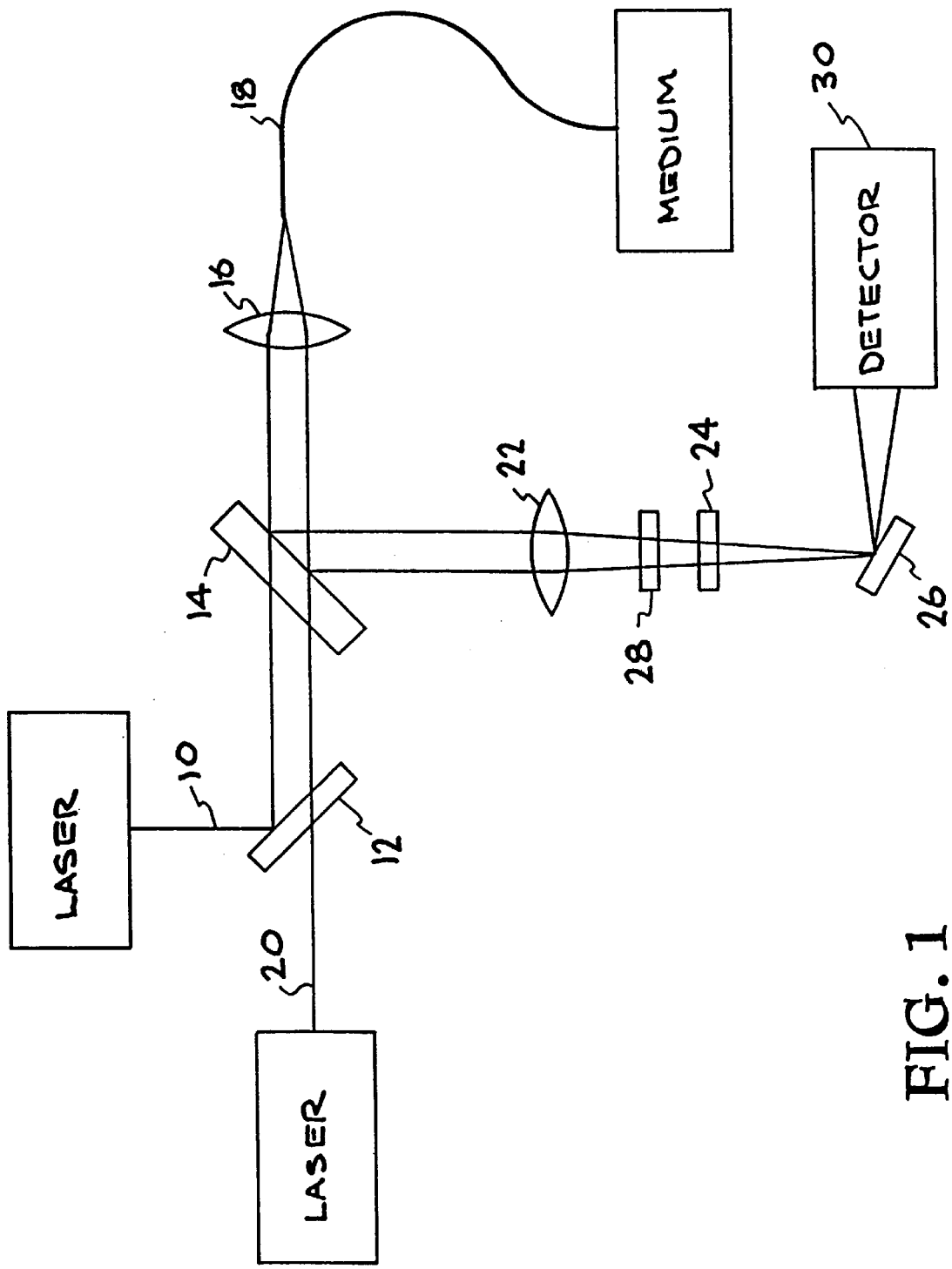
FIG. 1 shows an embodiment of the present invention.

An embodiment of the present invention is shown in FIG. 1. A laser system provides a laser beam 10 for bubble generation. This beam is reflected from a dichroic mirror or beamsplitter 12, passes through beamsplitter 14, (on a mirror 14 with a hole) and is focused by lens 16 into the proximal end of fiber optic 18. The distal end of this fiber is positioned for the delivery of laser light into a medium, such as near a thrombus within the vasculature. A second laser system provides a laser beam 20 for bubble detection. Laser beam 20 passes through beamsplitters 12 and 14 and is focused by lens 16 into fiber optic 18. As laser beam 10 forms bubbles in the liquid medium, laser beam 20 is variably reflected (Fresnel reflection) by the fiber-bubble interface at the distal end of fiber optic 18. This reflected light propagates back toward the proximal end of fiber optic 18, to exit and be collected by lens 16. A portion of this collected beam is reflected by beamsplitter 14, and is passed through polarizer 28, focused by lens 22, and passed through filter 24 onto grating 26. Other surfaces within this system also generate back reflected light, e.g., the dominant cause of unwanted back reflected light is the focusing lens 16 and the proximal surface of fiber optic 18. A properly oriented linear polarizer 28 rejects the linearly polarized reflected laser light from these surfaces while transmitting the randomly polarized light emerging from the optical fiber 18. A component of laser beam 10 also propagates back toward beamsplitter 14, to be focused by lens 22 and passed through polarizer 28. Filter 24 eliminates a portion of this bubble generating light. Grating 26 spatially separates the two wavelengths produced one each by laser beam 10 and laser beam 20. Detector 30 is generally positioned to receive light only from laser beam 20.

Figure 2A:
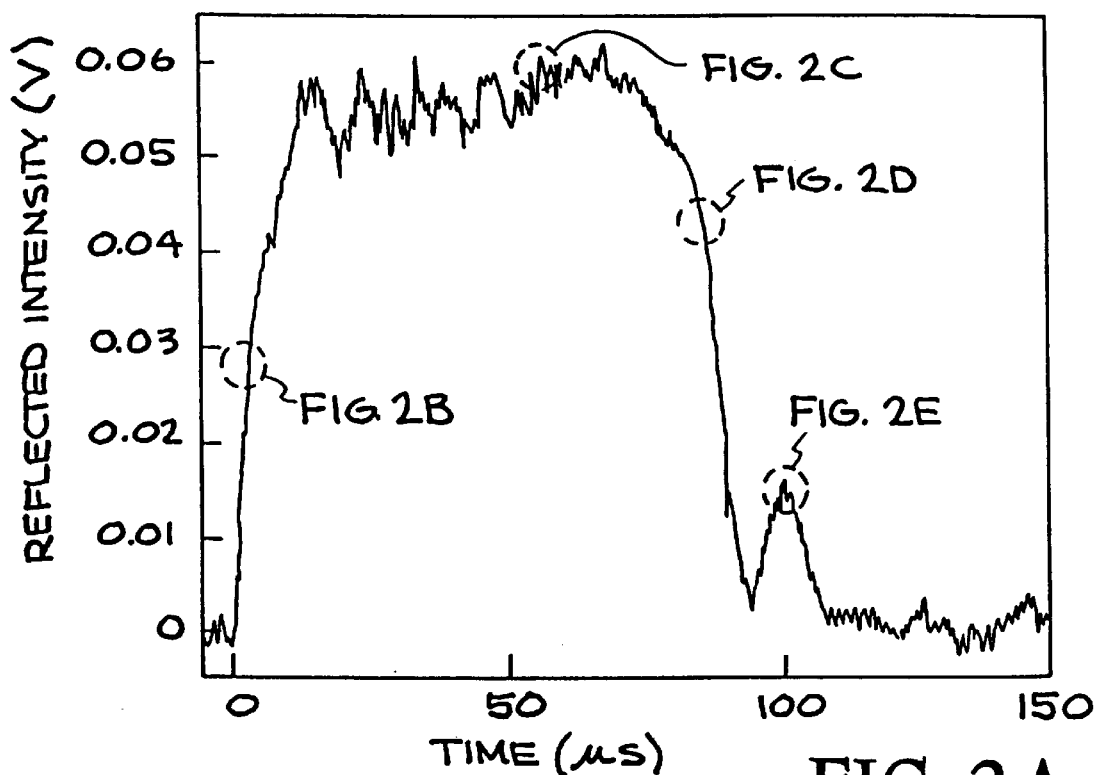
FIG. 2A shows the typical output from the detector of FIG. 1 during bubble formation and collapse.
Figure 2B:
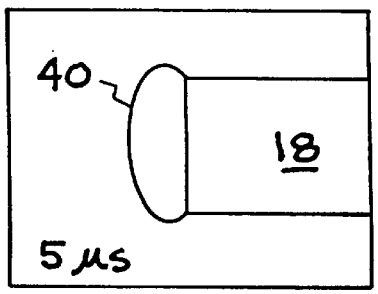
FIGS. 2B–E show the bubble growth and collapse at times of 5 µs, 55 µs, 85 µs and 100 µs respectively.
Figure 3:
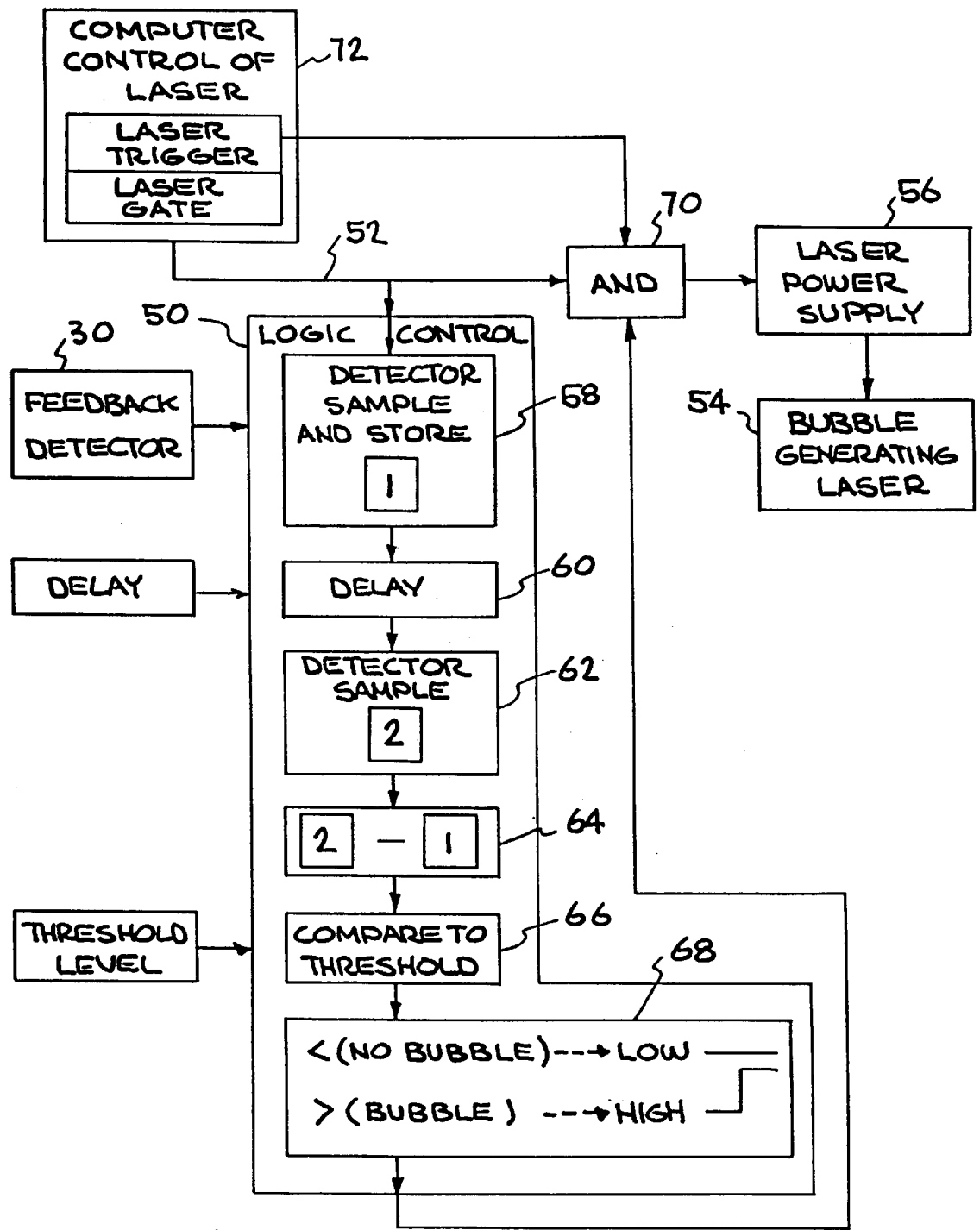
FIG. 3 shows a flowchart of the logic control elements of an embodiment of the feedback system of the invention.

FIG. 2A shows the signal emitted by the detector 30. This signal is delivered to the logic control electronics 50 which provide the feedback information, as shown in FIG. 3. The magnitude and temporal history of the light arriving at the detector, and thus the detector output signal, yield important information about the status of bubble formation and material properties at the distal tip of the fiber. A typical output from the detector during bubble formation and collapse is shown in FIG. 2A. Once a bubble forms at the fiber tip, the detector signal increases in magnitude as more light is reflected back into the fiber. FIG. 2B shows the formation of a bubble 40 at the tip of fiber 18 at 5 µs. A simple determination of bubble or no bubble can be made by comparing the signal before the therapeutic laser is fired and shortly thereafter, for example 10 µs. A trigger signal 52, as shown in FIG. 3, to the therapeutic laser 54 (and its associated power supply 56) can also be delivered to the logic control electronics 50 of the feedback device. This signal can trigger the feedback system to obtain a sample 58 from the detector 30 output immediately before the laser 54 is pulsed. A second sample 62 is taken at a predetermined delay 60 and compared to the first, as shown in block 64. If a preset threshold is surpassed, as shown at block 66, one can assume a bubble was formed. If no bubble was formed, either there was insufficient laser energy supplied or insufficient absorption due to a diluted sample or improper placement of the fiber tip, for example. This information could be used to temporarily turn off the laser, as shown at block 68, preventing useless delivery of energy. As shown at block 70, the laser trigger and laser gate signal from the laser computer control 72 and the logic control signal must be present before the bubble generating laser 54 can fire.

Figure 2C:
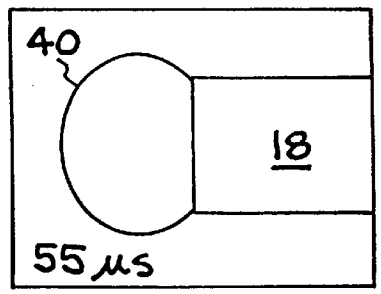
Figure 2D:
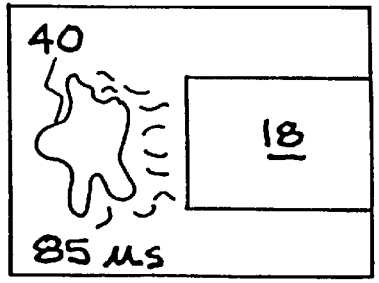
Figure 2E:
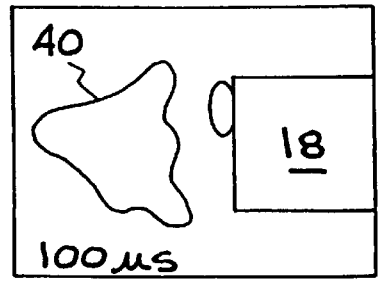
Figure 4:
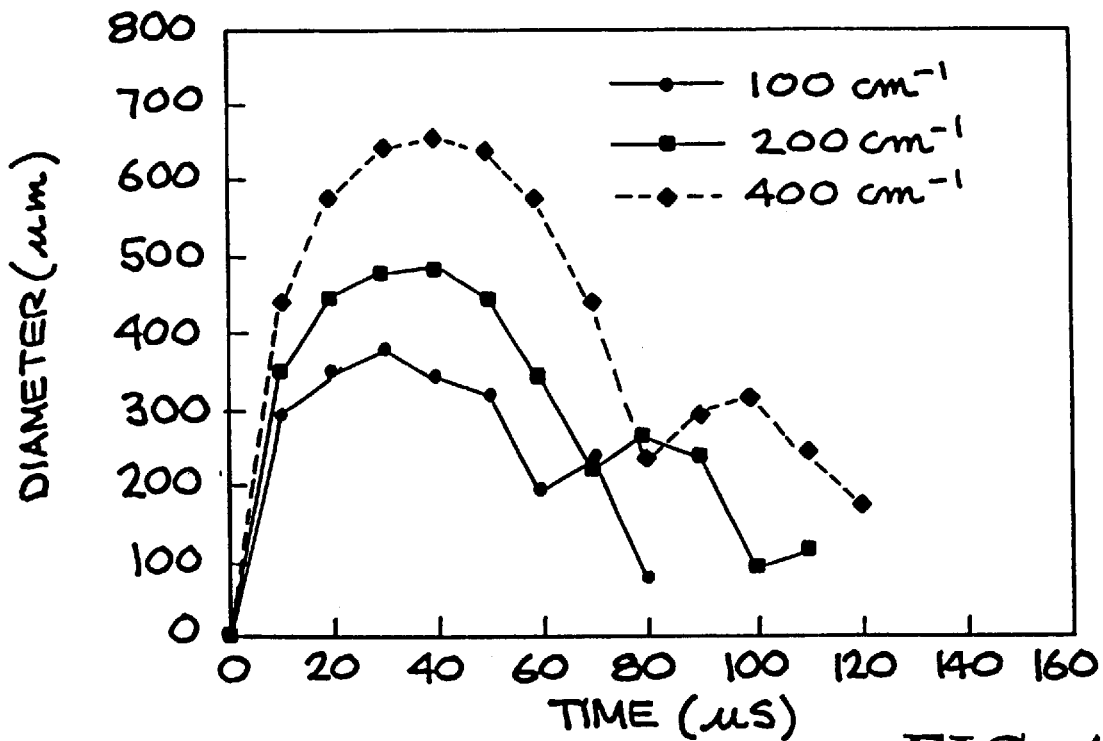
FIG. 4 shows data on bubble lifetime.

One can see from the sample trace (FIG. 2A) that the lifetime of the bubble can be determined from the duration of the increased detector signal. The detector signal can be sampled at multiple times to determine when the signal returns to baseline. FIGS. 2C–E show the bubble 40 growth and collapse at times of 55 $\mu$s, 85 $\mu$s and 100 $\mu$s respectively. Alternatively a timing circuit can be triggered upon surpassing a positive edge threshold and terminated upon a negative edge. This will yield data on the lifetime of a bubble which directly correlates to maximum bubble diameter (FIG. 4).

Figure 5:
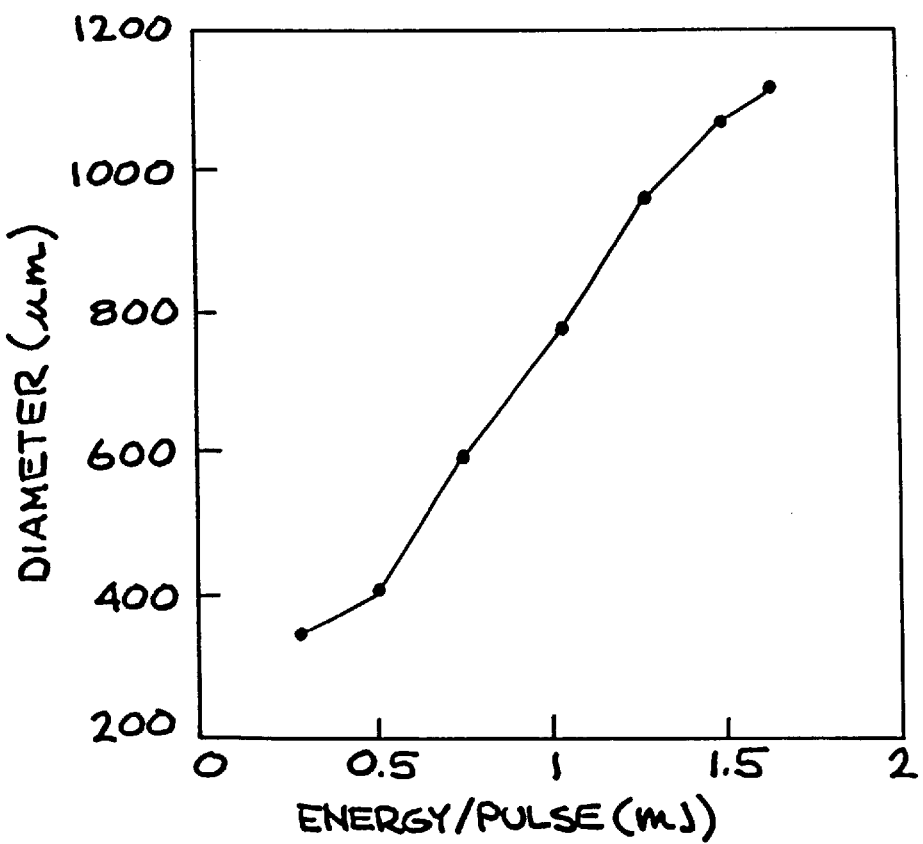
FIG. 5 shows data on bubble diameter versus energy/pulse.

Referring to FIG. 5, the bubble size is a function of the energy density (laser energy, spot size, and penetration depth) and the material properties. As the intensity of the reflected light depends on the index of refraction difference between the fiber and the surrounding media, tissue discrimination may be achieved by analyzing the detector signal. Biological tissues have indices of refraction that vary between approximately 1.33 to 1.5. Depending on the choice of optical fiber material (n$\approx$1.4-1.5), the percentage of reflected light due solely to Fresnel reflection at the fiber tip can be made to vary between 0 and 0.3%. By monitoring the detector signal, having a prior calibration curve (for index of refraction), and prior knowledge of potential tissues encountered, a user can distinguish which material is immediately proximal to the fiber tip. The use of additional probing wavelengths would make tissue discrimination easier as different wavelengths can have dramatically different optical properties (index of refraction, absorption, scattering, anisotropy) in tissues. The returned and detected signals from two or more probing wavelengths can be ratioed to give an indication of material type. For example, to discriminate whether a probe is immersed in blood or proximal to an artery wall, a wavelength strongly absorbed by blood (blue wavelength) and a wavelength poorly absorbed by both (red) may be used. When the fiber is immersed in blood, the ratio of the red light to the strongly absorbed and less scattering blue light should be greater than when the fiber is abutting the vessel. In this manner, intelligent choices for laser wavelengths can be made with respect to the likely target tissues and calibration curves could be generated. A 'smart' laser system could be provided these data to determine which tissue is being irradiated and alter the irradiation parameters (wavelength, pulse duration, energy/pulse, power, etc.) to achieve a desired effect or prevent undesirable consequences. A laser could be tuned to match the strongest absorption of the target material or could be disabled when an inappropriate target is present. A computer could be used to interpret this data and control the laser or these tasks could be performed by timing, level detection, and logic circuits.

In one embodiment of the invention, a feedback system may be included in a laser-based method of disrupting thrombus as a treatment for stroke. The treatment laser may consist of a pulsed laser. As minimal thermal energy could initiate complications and further damage, irradiation should be limited to the extent possible. If the treatment laser is not producing the desired effect it should be prevented from continued operation. The present feedback system, incorporating a continuous-wave low-power laser, monitors the status at the distal end of the fiber optic delivery system. If no significant change in detector signal is observed immediately prior to, and several microseconds after, the treatment pulse, then the feedback system blocks delivery of the treatment laser. After a duration, another treatment pulse is given and the bubble monitor probes for positive indication of a bubble. When a bubble is detected, it is assumed the laser is interacting properly with the target media and the treatment is allowed to continue. In this manner, wasteful and potentially damaging deposition of heat is prevented.

Applications envisioned for this invention include any method or procedure where the detection of vapor or cavitation bubbles is desirable. Applications may include bubble diagnostic and/or feedback mechanism during:

Laser-based treatment (e.g. Optical Acoustic Thrombolysis) of vascular occlusions that lead to ischemic stroke. This technology can lyse thrombus and lead to reperfusion of the affected cerebral tissue.

Laser-based treatment (e.g. Optical Acoustic Thrombolysis) of cerebral vasospasm. This technology can relax vaso-constriction leading to restoration of normal perfusion and therefore prevent further transient ischemic attacks or other abnormal perfusion situations.

Laser-based treatment (e.g. Optical Acoustic Thrombolysis) of cardiovascular occlusions. This technology can lyse thrombus or remove atherosclerotic plaque from arteries.

Laser-based treatment (e.g. Optical Acoustic Thrombolysis) of stenoses of the carotid arteries.

General restoration of patency in any of the body's luminal passageways wherein access can be facilitated via percutaneous insertion of optical fibers and subsequent vaporization driven ablation.

Any vaporization or cavitation based procedure using lasers or other means of generating vapor bubbles.

An embodiment of the invention incorporates a catheter containing an optical fiber. The optical fiber is coupled at the proximal end to a high repetition rate laser system which injects pulses of light along the beampath of laser beam 110 as described in FIG. 1. The light emerging from the fiber at the distal end is absorbed by the fluid surrounding the catheter. This fluid may be blood, a biological saline solution containing an absorbing dye, a thrombolytic pharmaceutical or thrombus itself. The optical fiber functions as a means of energy transmission such that the optical energy produced by the laser is delivered to the end of the fiber. The high repetition rate laser light emerging from the distal end of the fiber optic has a pulse frequency within the range of 10 Hz to 100 kHz, a wavelength within the range of 200 nm to 5000 nm and an energy density within the range of 0.01 J/cm$^2$ to 4 J/cm$^2$, or up to 50 J/cm$^2$, if dictated by a small optical fiber diameter. The energy applied is maintained below 5 milli-Joules, and preferably less than one milli-Joule. In one embodiment, the pulse frequency is within the range of 5 kHz to 25 kHz. Alternately, a lower end of the pulse frequency range may be 100 Hz, with an upper end of the range being 100 kHz.

Figure 6A:
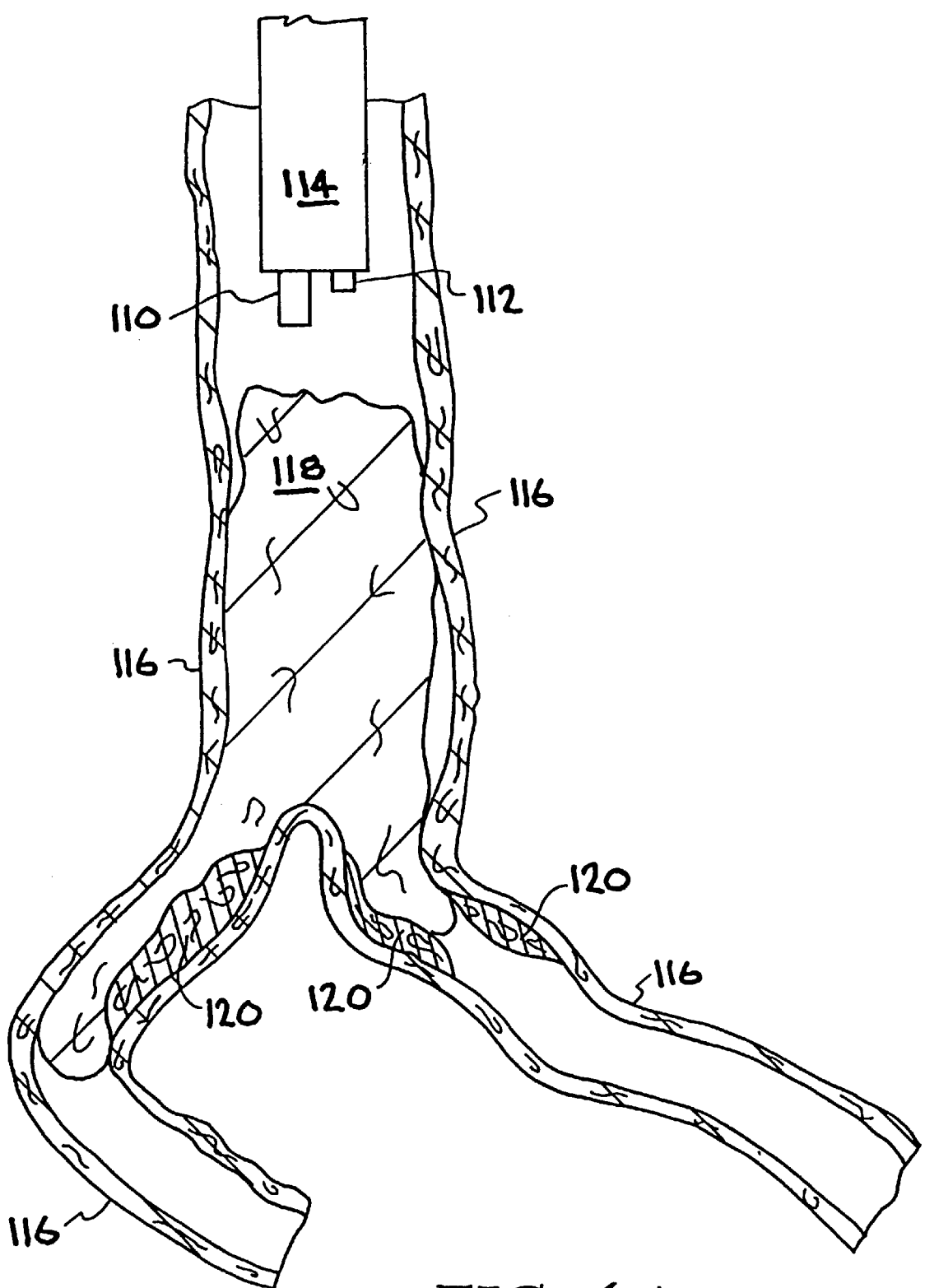
FIG. 6A shows a sketch of an application the present invention in an optical fiber-based opto-acoustic thrombolysis catheter.
Figure 6B:
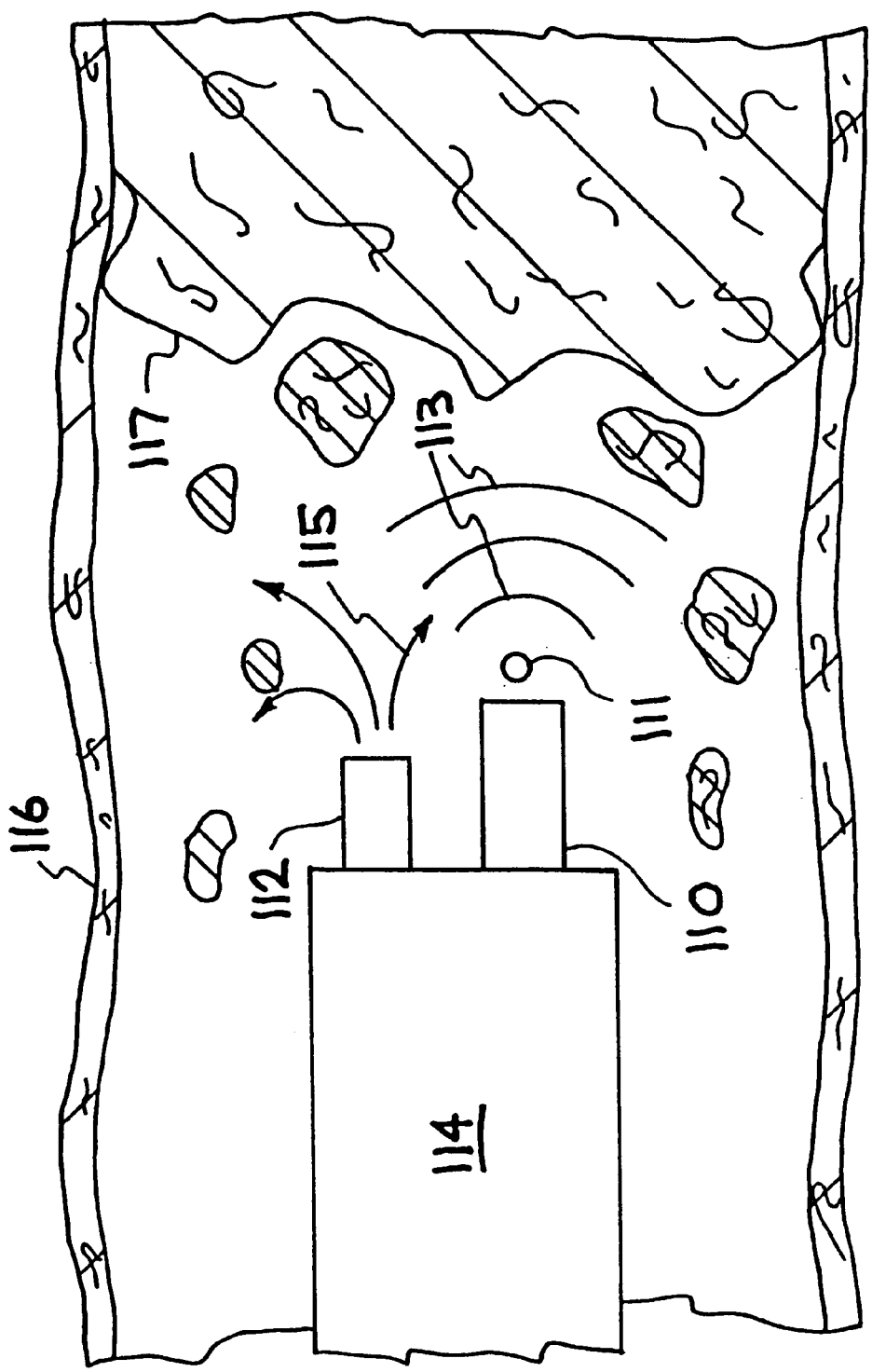
FIG. 6B depicts the ultrasonic dissolution of a blockage using an adjunct fluid.

Lysis of thrombus, atherosclerotic plaque or any other occluding material in the tubular tissue is facilitated by an ultrasonic radiation field created in the fluids near the occlusion. As an adjunct treatment, a working channel which surrounds or runs parallel to the optical fiber may be used to dispense small quantities of thrombolytic drugs to facilitate further lysis of any significantly sized debris (>5 $\mu$m dia. particles) left over from the acoustic thrombolysis process. The conversion of optical to acoustic energy may proceed through several mechanisms that may be thermoelastic, thermodynamic or a combination of these. FIG. 6A shows an optical fiber 110 with a parallel working channel 112, where both the fiber 110 and the working channel 112 are both located within a catheter 114 which has been inserted into a blood vessel 116. The distal end of fiber 110 is placed near thrombus 118 and/or stenotic plaque 120 within blood vessel 116. In FIG. 6B, fiber 110 delivers laser light to produce a collapsing cavitation bubble 111 and the resulting expanding acoustic wave 113. A parallel working channel 112 in catheter 114 delivers an adjunct fluid 115 to aid in the removal of occlusion 117 from inside blood vessel 116.

Figure 7A:
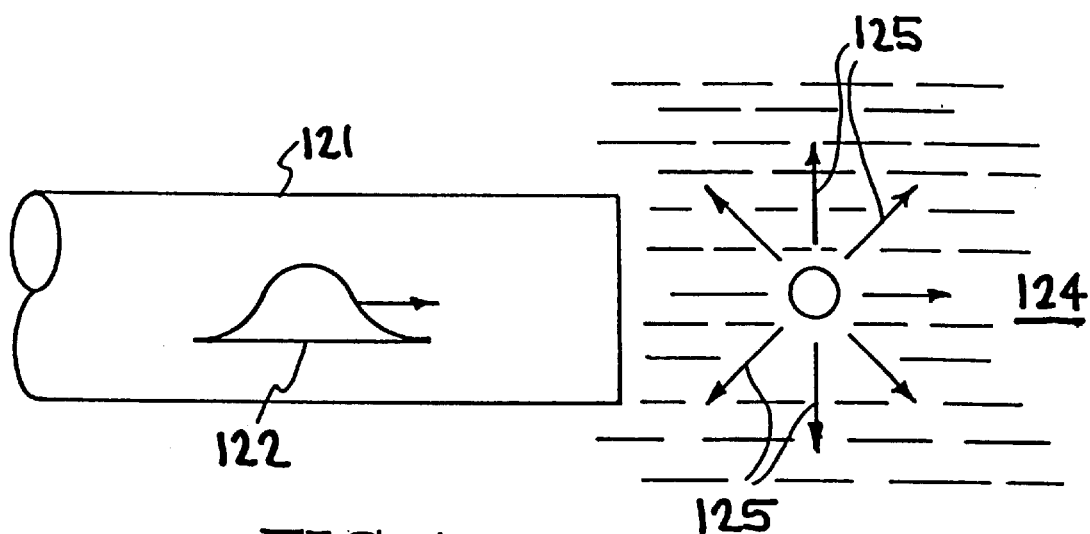
FIGS. 7A–C depict the thermo-elastic operation as a method of bubble formation.
Figure 7B:
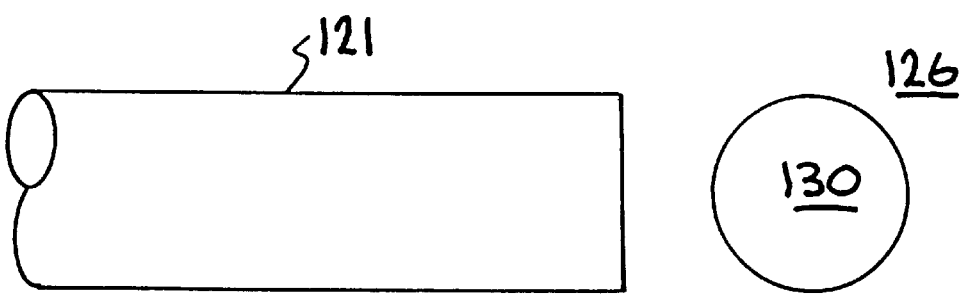
Figure 7C:
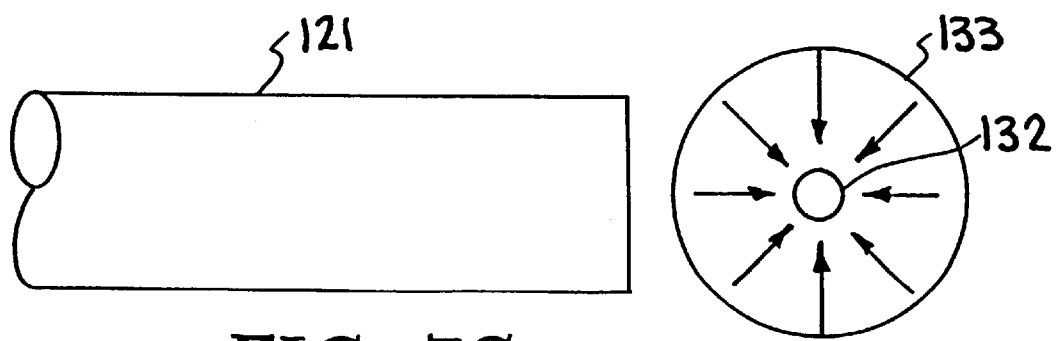

As depicted in FIGS. 7A–C, in the thermoelastic mode, through fiber optic 121, each laser pulse 122 delivers a controlled level of energy in the fluid 124 which creates a large thermoelastic stress in a small volume of the fluid. The expanding direction of this stress is indicated by arrows 125 in FIG. 7A. The volume of fluid 124 which is heated by the laser pulse 122 is determined by the absorption depth of the laser light in the fluid 124, and must be controlled to produce a desired size. For example, an appropriate size may be the fiber diameter, or a distance comparable to some fraction of the vessel containing the occlusion. This can be adjusted by controlling the laser wavelength or the composition of the fluid such that most of the laser energy is deposited in a fluid depth of the desired size. The laser pulse duration is ideally short enough to deposit all of the laser energy into the absorbing fluid in a time scale shorter than the acoustic transit time across the smallest dimension of absorbing region. This is an isochoric (constant volume) heating process. For an absorption volume of approximately 100 $\mu$m in diameter the acoustic transit time is approximately 70 ns, so the deposition time must be significantly less than this, e.g., around 10 ns.

The absorbing fluid responds thermoelastically to the deposition of energy such that a region of high pressure is created in the fluid in the heated volume. The boundary of the high pressure zone decays into a pattern of acoustic waves: a compression wave propagates away from the energy deposition region (diverging wave front) and a rarefaction wave propagates towards the center of the energy deposition region (converging wave front). When the rarefaction wave converges on the center of the initial deposition region, it creates a region 126 of tensile stress that promotes the formation of a cloud of cavitation bubbles which coalesce to form a larger bubble 130. Eventually, the cavitation bubble collapses (132), resulting in an expanding acoustic wave 133. Collapse and subsequent rebound of the cavitation bubble will generate acoustic impulses in the surrounding fluid, which will carry off a portion of the energy of the cavity. The collapse and rebound processes take place on a time scale governed principally by the fluid density and the maximum size of the initial cavity. The first collapse and rebound will be followed by subsequent collapse and rebound events of diminishing intensity until the energy of the cavity is dissipated in the fluid. Subsequent laser pulses are delivered to repeat or continue this cycle and generate an ultrasonic radiation field at a frequency or frequencies determined by the laser pulse frequency.

To summarize, a device operating through the first mode produces an ultrasonic radiation field in the fluid by: (i) depositing laser energy in a volume of fluid comparable to the fiber dimension in a time scale of duration less than the acoustic transit time across this dimension (as controlled by choice of laser wavelength and absorbing fluid as the case may be); (ii) controlling the laser energy such that the maximum size of the cavitation bubble is approximately the same as that the fiber diameter; and (iii) pulsing the laser at a repetition rate such that multiple cycles of this process generate an acoustic radiation field in the surrounding fluid; resonant operation may be achieved by synchronizing the laser pulse repetition rate with the cavity lifetime. Typical operation leads to a fluid-based transducer that cycles at 1-100 kHz with a reciprocating displacement of 100-200 $\mu$m (for typical optical fiber dimensions). This displacement is very similar to that found in mechanically-activated ultrasound angioplasty devices.

Figure 8A:
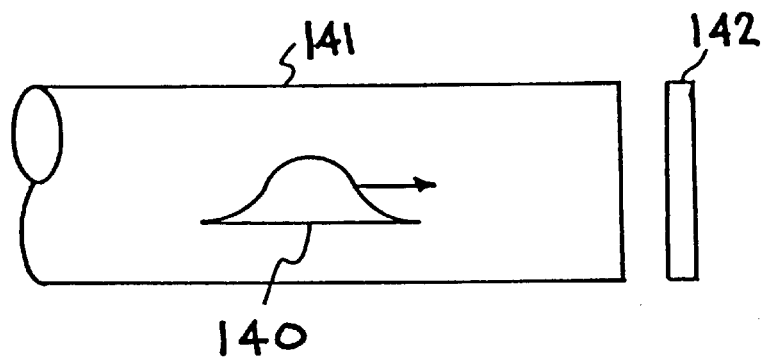
FIGS. 8A–C depict the superheated vapor expansion mode as a method of bubble formation.
Figure 8B:
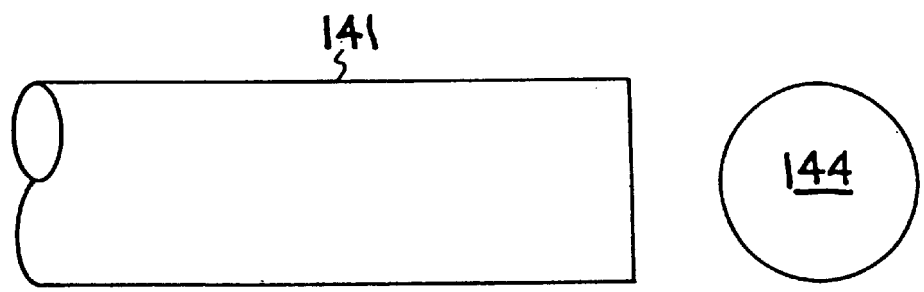
Figure 8C:
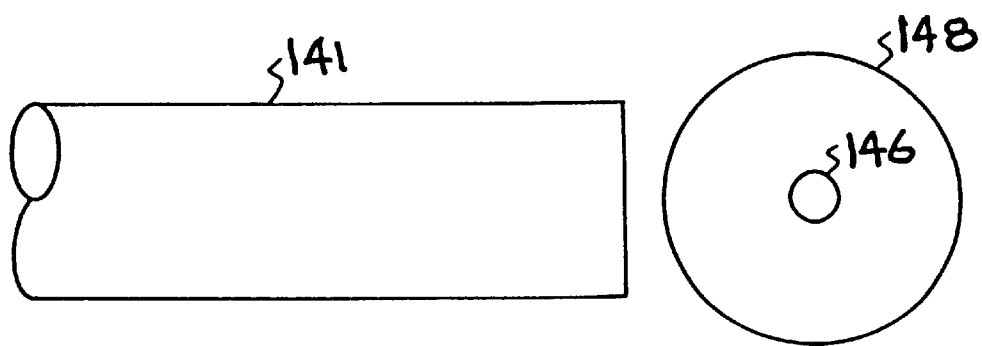

In the superheated vapor expansion mode, as shown in FIGS. 8A–C, in fiber optic 141, each laser pulse 140 delivers a controlled level of energy in the fluid within an absorption depth which is very small compared to the characteristic size of the vessel containing the catheter, or even small compared to the fiber diameter. The absorption depth may also be small compared to the distance that a sound wave travels in the duration of the laser pulse. The laser energy deposits a sufficient level of energy to heat most of the fluid within the absorption depth well above the vaporization temperature of the fluid at the ambient pressure. In the process of depositing the laser energy, a thermoelastically-generated acoustic wave is launched in the fluid, which propagates out from the heated region. On time scales longer than 1 $\mu$s, the superheated fluid 142 undergoes vaporization, which creates a bubble of vapor. As the fluid vaporizes, its volume 144 increases by a large factor.

The laser pulse duration need not be restricted to times as short as in the thermoelastic mode since the bubble expansion is nearly an isobaric process; however, the laser pulse duration should be shorter than the bubble expansion time, and it should be much shorter than a typical thermal relaxation time for the superheated region. (According to the Rayleigh bubble collapse theory the bubble lifetime in water is approximately 25 $\mu$s for a 50 $\mu$m diameter bubble; thermal relaxation occurs on a few hundred microsecond time scale, so the laser pulse should be several microseconds or less in duration). The vapor bubble expands up to a maximum radius which depends on the vapor pressure initially created in the fluid and the fluid properties. At the maximum bubble radius, the vapor pressure in the expanded bubble has dropped to well below the ambient pressure and the bubble 146 undergoes collapse, resulting in an expanding acoustic wave 148. Rebound and subsequent collapse events may take place following the first collapse. The bubble expansion and collapse couples acoustic energy into the fluid. Subsequent laser pulses are delivered to repeat or continue this cycle and generate an ultrasonic radiation field at a frequency or frequencies determined by the laser pulse frequency. Similar to the first mode, a resonant operation may be achieved by matching the laser pulse period to the lifetime of the vapor bubble.

To summarize, a device operating through the second mode produces an ultrasonic radiation field in the fluid by: (i) depositing laser energy in a small volume of fluid (as controlled by choice of laser wavelength and absorbing fluid as the case may be); (ii) controlling the laser energy such that the maximum size of the vapor bubble such that the bubble does not damage the surrounding tissues; and (iii) pulsing the laser energy at a repetition rate such that multiple cycles of the bubble generation and collapse process generates an acoustic radiation field in the surrounding fluid. Unlike the first mode, the delivery time is not a significant issue, so longer pulse duration lasers (up to several $\mu$s) may be useful.

For either mode of operation the laser wavelength, laser pulse duration and laser absorption depth must be precisely controlled such that an adequate acoustic response is obtained with a minimum of laser pulse energy. For the first mode this entails matching the absorption volume to a characteristic dimension of the system such as the fiber diameter or some fraction of the vessel diameter, and using a short laser pulse (less than 20 ns). For the second mode this entails depositing the laser energy in a very small absorption depth to achieve a sufficient level of superheat in a small fluid mass such as can be accommodated by a small energy budget and without creating a vapor bubble so large as to be damaging to the surrounding tissues.

These opto-acoustic modes of coupling laser energy into acoustic excitations in tissues include a number of features. Low to moderate laser pulse energy combined with high repetition rate avoids excessive tissue heating or intense shock generation. Localized absorption of the laser energy occurs. Laser energy may interact thermoelastically or thermodynamically with the ambient fluids. An acoustic radiation field is generated by repeated expansion and collapse of a bubble at the tip of the fiber. Resonant operation may be achieved by matching the laser pulse period to the lifetime of the generated bubble. Soft fibrous occlusions (thrombus) may be disrupted by generating the bubbles directly within the thrombus.

Control and/or manipulation of the spatial and temporal distribution of energy deposited in the fluid at the fiber tip, as shown in FIG. 1 and FIG. 3, can be used to modify the near field acoustic radiation pattern, for example, to concentrate acoustic energy on an object in proximity to the fiber, or to distribute the acoustic radiation more uniformly. Techniques based on this strategy will be most successful for a special case of thermoelastic response (first mode) where the laser pulse duration is short and the fluid absorption is also relatively strong, such that the laser energy is deposited in a thin layer adjacent to the surface of the fiber tip. For example, by forming a concave surface on the fiber tip, the optical energy is deposited in the fluid in a similar shaped distribution. Acoustic waves emitted from this concave distribution will tend to focus to a point at a distance R from the fiber tip, where R is the radius of curvature of the concave surface. A planar fiber tip will generate an initially planar acoustic wavefront in proximity to the fiber tip. A convex fiber tip will produce a diverging spherical wavefront which will disperse the acoustic energy over a larger solid angle. Another means of modifying the near field radiation pattern may be to use a fiber bundle through which the laser energy is delivered, and control the temporal distribution of deposited laser energy. The laser energy may be arranged to arrive at individual fiber strands in the catheter tip at different times, which, in combination with the different spatial positions of these individual strands, can be adjusted to control the directionality and shape of the acoustic radiation pattern, similar to phased-array techniques used in radar.

Commercial fibers are usually jacketed to protect them from the environment. "Bare" or unjacketed fibers are available. It is helpful to use coatings on fibers to make them slide more easily through catheters. A variable diameter optical fiber allows for greater physical strength at the proximal end and greater access at the distal end. This can be accomplished through modifying existing fibers (stripping the protective sheath from around the core) or by making custom fibers. Custom fabrication can be accomplished by varying the extrusion or draw rate for the fiber. Glass or plastic composition can be changed as a function of drawing the fiber so that greater control of the fiber from a distal end is achieved without sacrificing optical quality. One particular instance of this is to treat the tip so that it is "soft," so the end will not jam in the catheter sheath. Also, shape memory in the tip allows steering of the fiber when it protrudes from the distal end of the catheter sheath.

The pulsed laser energy source used by this invention can be based on a gaseous, liquid or solid state medium. Rare earth-doped solid state lasers, ruby lasers, alexandrite lasers, Nd:YAG lasers and Ho:YLF lasers are all examples of lasers that can be operated in a pulsed mode at high repetition rate and used in the present invention. Any of these solid state lasers may incorporate non-linear frequency-doubling or frequency-tripling crystals to produce harmonics of the fundamental lasing wavelength. A solid state laser producing a coherent beam of ultraviolet radiation may be employed directly with the invention or used in conjunction with a dye laser to produce an output beam which is tunable over a wide portion of the ultraviolet and visible spectrum. Tunability over a wide spectrum provides a broad range of flexibility for matching the laser wavelength to the absorption characteristics of the fluids located at the distal end of the catheter. The output beam is coupled by an optical fiber to the surgical site through, for example, a percutaneous catheter. In operation, a pulsed beam of light drives the ultrasonic excitation which removes and/or emulsifies thrombus or atherosclerotic plaque with less damage to the underlying tissue and less chance of perforating the blood vessel wall than prior art devices.

Various other pulsed lasers can be substituted for the disclosed laser sources. Similarly, various dye materials and configurations can be used in the dye laser. Configurations other than a free-flowing dye, such as dye-impregnated plastic films or cuvette-encased dyes, can be substituted in the dye laser. The dye laser can also store a plurality of different dyes and substitute one for another automatically in response to user-initiated control signals or conditions encountered during use (e.g. when switching from a blood-filled field to a saline field or in response to calcific deposits). Suitable dyes for use in the dye laser components of the invention include, for example, P-terphenyl (peak wavelength 339); BiBuQ (peak wavelength: 385); DPS (peak wavelength: 405); and Coumarin 2 (peak wavelength: 448).

In yet another embodiment the pulsed light source may be an optical parametric oscillator (OPO) pumped by a frequency-doubled or frequency-tripled solid-state laser. OPO systems allow for a wide range of wavelength tunability in a compact system comprised entirely of solid state optical elements. The laser wavelength in OPO systems may also be varied automatically in response to user-initiated control signals or conditions encountered during use.

Catheters, useful in practicing the present invention, can take various forms. For example, one embodiment can consist of a catheter having an outer diameter of 3.5 millimeters or less, preferably 2.5 millimeters or less. Disposed within the catheter is the optical fiber which can be a 400 micron diameter or smaller silica (fused quartz) fiber such as the model SG 800 fiber manufactured by Spectran, Inc. of Sturbridge, Mass. The catheter may be multi-lumen to provide flushing and suction ports. In one embodiment the catheter tip can be constructed of radio-opaque and heat resistant material. The radio-opaque tip can be used to locate the catheter under fluoroscopy.

Changes and modifications in the specifically described embodiments can be carried out without departing from the scope of the invention, which is intended to be limited by the scope of the appended claims.

What is claimed is:

1. A method for detecting the presence of a bubble, comprising:

inserting a fiber optic into a liquid ambient medium, wherein said fiber optic comprises a proximal end and a distal end;

coupling a first beam of laser light from a high repetition laser system into said proximal end, wherein said first beam of laser light emerges from said distal end within said liquid ambient medium;

transmitting a second beam of laser light into said proximal end, wherein said second beam of light is partially reflected by said distal end to produce a reflected second beam, wherein as said bubble forms and grows at said distal end, the amount of light reflected by said distal end increases;

detecting said reflected second beam to produce a detected signal;

storing a first sample of said detected signal before said high repetition laser system fires said first beam of laser light;

storing a second sample of said detected signal a predetermined delay after said high repetition laser system fires said first beam of laser light; and subtracting said second sample from said first sample to obtain a sample difference;

such that if said sample difference is greater than a predetermined threshold level, continuing to fire said first beam of laser light from said high repetition laser system; or such that if said sample difference is less than said predetermined threshold level, controlling said high repetition laser system according to a method selected from a group consisting of (i) discontinuing firing said first beam of laser light from said high repetition laser system for at least a period of time, and (ii) increasing the power of said first laser beam, up to a predetermined power, until said bubble forms.

2. A method for detecting the presence of a bubble, comprising:

transmitting a beam of laser light through a fiber optic comprising a proximal end and a distal end, wherein a portion of said beam of laser light is reflected by said distal end, wherein the amount of light within said reflected portion of said beam of laser light increases as said bubble forms and grows at said distal end;

detecting said reflected portion of said beam of laser light to produce a detected signal;

storing a first sample of said detected signal before a bubble formation laser system fires said first beam of laser light;

storing a second sample of said detected signal a predetermined delay after said bubble formation laser system fires said first beam of laser light; and subtracting said second sample from said first sample to obtain a sample difference;

such that if said sample difference is greater than a predetermined threshold level, continuing to fire said first beam of laser light from said bubble formation laser system; or such that if said sample difference is less than said predetermined threshold level, controlling said bubble formation laser system according to a method selected from a group consisting of (i) discontinuing firing said first beam of laser light from said bubble formation laser system for at least a period of time, and (ii) increasing the power of said first laser beam, up to a predetermined power, until said bubble forms.

3. The method of claim 2, wherein a user, having prior information on indices of refraction and prior knowledge of potential materials encountered, can distinguish which material is immediately proximal to the fiber tip.

4. The method of claim 3, wherein said plurality of samples are taken with at least two alternating wavelengths, wherein different wavelengths have different optical properties in materials, said optical properties selected from the group of index of refraction, absorption, scattering, and anisotropy, wherein detected signals from at least two alternating wavelengths are ratioed to give an indication of material type.

5. An apparatus for detecting the presence of a bubble, comprising:

means for inserting a fiber optic into a liquid ambient medium, wherein said fiber optic comprises a proximal end and a distal end;

means for coupling a first beam of laser light from a high repetition laser system into said proximal end, wherein said first beam of laser light emerges from said distal end within said liquid ambient medium;

means for transmitting a second beam of laser light into said proximal end, wherein said second beam of light is partially reflected by said distal end to produce a reflected second beam wherein as said bubble forms and grows at said distal end, the amount of light reflected by said distal end increases;

means for detecting said reflected second beam to produce a detected signal;

means for storing a first sample of said detected signal before said high repetition laser system fires said first beam of laser light;

means for storing a second sample of said detected signal a predetermined delay after said high repetition laser system fires said first beam of laser light;

means for subtracting said second sample from said first sample to obtain a sample difference; and means for controlling said high repetition laser system based on said sample difference.

6. An apparatus for detecting the presence of a bubble, comprising:

means for transmitting a beam of laser light through a fiber optic comprising a proximal end and a distal end, wherein a portion of said beam of laser light is reflected by said distal end, wherein the amount of light within said reflected portion of said beam of light increases as said bubble forms and grows at said distal end;

means for detecting said reflected portion of said beam of laser light to produce a detected signal;

means for storing a first sample of said detected signal before a bubble formation laser system fires said first beam of laser light;

means for storing a second sample of said detected signal a predetermined delay after said bubble formation laser system fires said first beam of laser light;

means for subtracting said second sample from said first sample to obtain a sample difference;

means for continuing to fire said first beam of laser light from said bubble formation laser system if said sample difference is greater than a predetermined threshold level; and means for controlling said bubble formation laser system, if said sample difference is less than said predetermined threshold level, according to a method selected from a group consisting of (i) discontinuing firing said first beam of laser light from said bubble formation laser system for at least a period of time, and (ii) increasing the power of said first laser beam, up to a predetermined power, until said bubble forms.

7. An apparatus for detecting the presence of a bubble, comprising:

means for combining a bubble formation laser beam and a bubble diagnostic laser beam to make them collinear;
a fiber optic comprising a proximal end and a distal end;
means for focusing said bubble formation laser beam and said bubble diagnostic laser beam into said proximal end of said fiber optic;
a detector;
means for directing light reflected from said distal end of said fiber optic onto said detector; and
a logic control system comprising means for analyzing a signal produced by said detector to detect the presence of said bubble.

8. The apparatus of claim 7, further comprising means for analyzing said signal produced by said detector to control a bubble formation laser.

9. The apparatus of claim 7, wherein said bubble diagnostic laser beam is produced by a laser selected from a group consisting of a diode laser, a dye laser and a HeNe laser.

10. The apparatus of claim 7, wherein said means for combining a bubble formation laser beam and a bubble diagnostic laser beam to make them collinear comprise a dichroic mirror.

11. The apparatus of claim 7, wherein said means for combining a bubble formation laser beam and a bubble diagnostic laser beam to make them collinear comprise a beamsplitter.

12. The apparatus of claim 7, wherein said means for directing light reflected from said distal end of said fiber optic onto said detector comprise a beamsplitter.

13. The apparatus of claim 7, wherein said means for directing light reflected from said distal end of said fiber optic onto said detector comprise a mirror with hole.

14. The apparatus of claim 7, wherein said means for directing light reflected from said distal end of said fiber optic onto said detector comprise a polarizer, filter and a grating to reject light from said bubble formation laser beam and primary surface reflections of said bubble diagnostic laser beam.

15. The apparatus of claim 7, wherein said means for directing light reflected from said distal end of said fiber optic onto said detector comprise a polarizer to reject light from said bubble formation laser beam and primary surface reflections of said bubble diagnostic laser beam.

16. The apparatus of claim 7, wherein said means for directing light reflected from said distal end of said fiber optic onto said detector comprise a filter to reject light from said bubble formation laser beam.

17. The apparatus of claim 7, wherein said means for directing light reflected from said distal end of said fiber optic onto said detector comprise a grating to reject light from said bubble formation laser beam.

18. The method of claim 3, wherein said material is distinguished by determining an index of refraction from the amount of light reflected at a wavelength within any sample of said detected signal and then correlating said index of refraction to a material.

19. The apparatus of claim 5, wherein said means for controlling said high repetition laser system comprises means for continuing firing said first beam of laser light from said high repetition laser system if said sample difference is greater than a predetermined threshold level; and means for discontinuing firing said high repetition laser system if said sample difference is less than said predetermined threshold level.

20. A method of using a fiber optic device within a body lumen having occlusive material therein, comprising:

inserting a distal end of a fiber optic into a fluid medium within the body lumen;
delivering a first beam of light to the distal end, such that the first beam interacts with the fluid medium to disrupt the occlusive material;
delivering a second beam of light to the distal end;
monitoring a reflection of the second beam into the distal end to obtain information selected from a group consisting of first information relating to any bubble at the distal end, second information relating to any material at the distal end, and any combination thereof, the first information selected from a group consisting of an absence or a presence of the bubble, a duration of the bubble, a size of the bubble, and any combination thereof, and the second information selected from a group consisting of a type of the material, an absorption characteristic of the material, a mechanical characteristic of the material, and any combination thereof; and
controlling the first beam based on the information.

21. The method of claim 20, wherein the body lumen is cardiovascular or cerebrovascular.

22. The method of claim 20, wherein the occlusive material is a thrombus or an atherosclerotic plaque.

23. The method of claim 20, wherein the fluid medium is blood, biological saline solution containing a light-absorbing dye, a thrombolytic pharmaceutical, or a thrombus.

24. The method of claim 20, wherein at least one of the first and second light beams is generated by a laser.

25. The method of claim 24, wherein the first beam is generated by a pulsed laser.

26. The method of claim 24, wherein the second beam is generated by a continuous-wave laser.

27. The method of claim 20, wherein the first beam is generated by a optical parametric oscillator.

28. The method of claim 20, wherein the interaction between the first beam and the fluid medium is light absorption.

29. The method of claim 20, wherein the interaction between the first beam and the fluid medium includes generation of a bubble.

30. The method of claim 20, wherein the disruption of the occlusive material is facilitated by an opto-acoustic mechanism, a thermoelastic mechanism, a thermodynamic mechanism, or any combination thereof.

31. The method of claim 20, wherein the disruption of the occlusive material is facilitated by a thrombolytic pharmaceutical.

32. The method of claim 20, wherein the disruption of the occlusive material includes emulsification, removal, lysis, or any combination thereof, of the occlusive material.

33. The method of claim 20, wherein said monitoring comprises monitoring a reflection of the second beam as represented by a signal having a DC component and an AC component, the AC component providing the first information.

34. The method of claim 20, wherein said controlling comprises discontinuing, at least temporarily, said delivering of the first beam.

35. The method of claim 20, wherein said controlling comprises continuing said delivering of the first beam.

36. The method of claim 20, wherein said controlling comprises controlling an irradiation parameter of the first beam.

37. The method of claim 20, wherein the bubble is formed by vaporization, cavitation, or any combination thereof.

38. A fiber optic device for treating a body lumen having occlusive material therein, comprising:

a fiber optic having a proximal end and a distal end, said fiber optic of a construction sufficient for insertion of the distal end into a fluid medium within the body lumen;

means for coupling a first beam of light and a second beam of light into the proximal end for delivery to the distal end, wherein the first beam is capable of interacting with the fluid medium to disrupt the occlusive material;

means for monitoring a reflection of the second beam into the distal end to obtain information selected from a group consisting of first information relating to any bubble at the distal end, second information relating to any material at the distal end, and any combination thereof, the first information selected from a group consisting of an absence or a presence of the bubble, a duration of the bubble, a size of the bubble, and any combination thereof, and the second information selected from a group consisting of a type of the material, an absorption characteristic of the material, a mechanical characteristic of the material, and any combination thereof; and means for controlling the first beam based on the information.

39. The device of claim 38, further comprising a catheter that contains the fiber optic, said catheter of a construction sufficient for insertion of a distal end thereof within the body lumen.

40. The device of claim 38, further comprising a working channel which surrounds or runs parallel to the fiber optic.

41. The device of claim 40, wherein said a working channel is a channel for delivery of a fluid which facilitates the disruption of the occlusive material.

42. The device of claim 40, further comprising a catheter that contains the fiber optic and the working channel, said catheter of a construction sufficient for insertion of a distal end thereof within the body lumen.

43. The device of claim 38, wherein the body lumen is cardiovascular or cerebrovascular.

44. The device of claim 38, wherein the occlusive material is a thrombus or an atherosclerotic plaque.

45. The device of claim 38, wherein the fluid medium is blood, biological saline solution containing a light-absorbing dye, a thrombolytic pharmaceutical, or a thrombus.

46. The device of claim 38, wherein at least one of the first and second light beams is generated by a laser.

47. The device of claim 46, wherein the first beam is generated by a pulsed laser.

48. The device of claim 46, wherein the second beam is generated by a continuous-wave laser.

49. The device of claim 38, wherein the first beam is generated by a optical parametric oscillator.

50. The device of claim 38, wherein interaction between the first beam and the fluid medium is light absorption.

51. The device of claim 38, wherein interaction between the first beam and the fluid medium includes generation of a bubble.

52. The device of claim 38, wherein disruption of the occlusive material is facilitated by an opto-acoustic mechanism, a thermoelastic mechanism, a thermodynamic mechanism, or any combination thereof.

53. The device of claim 38, wherein disruption of the occlusive material is facilitated by a thrombolytic pharmaceutical.

54. The device of claim 38, wherein disruption of the occlusive material includes emulsification, removal, lysis, or any combination thereof, of the occlusive material.

55. The device of claim 38, wherein said means for monitoring comprises means for monitoring a reflection of the second beam as represented by a signal having a DC component and an AC component, the AC component providing the first information.

56. The device of claim 38, wherein said means for controlling comprises means for discontinuing, at least temporarily, delivery of the first beam.

57. The device of claim 38, wherein said means for controlling comprises means for continuing delivery of the first beam.

58. The device of claim 38, wherein said means for controlling comprises means for controlling an irradiation parameter of the first beam.

59. The device of claim 38, wherein the bubble is formed by vaporization, cavitation, or any combination thereof.

60. A method for detecting the presence of a bubble, comprising:

inserting a fiber optic into a liquid ambient medium, wherein said fiber optic comprises a proximal end and a distal end;

coupling a first beam of laser light from a laser system into said proximal end, wherein said first beam of laser light emerges from said distal end within said liquid ambient medium;

transmitting a second beam of laser light into said proximal end, wherein said second beam of light is partially reflected by said distal end to produce a reflected second beam, wherein as said bubble forms and grows at said distal end, the amount of light reflected by said distal end increases;

detecting said reflected second beam to produce information; and controlling said laser system based on said information.

61. An apparatus for detecting the presence of a bubble, comprising:

means for transmitting a beam of laser light through a fiber optic comprising a proximal end and a distal end, wherein a portion of said beam of laser light is reflected by said distal end, wherein the amount of light within said portion of said beam of light increases as said bubble forms and grows at said distal end;

means for detecting said portion of said beam of laser light to produce information; and means for controlling a bubble formation laser system based on said information.

* * * * *